United States Patent
Leewood et al.

(10) Patent No.: US 9,517,123 B2
(45) Date of Patent: Dec. 13, 2016

(54) ENDOVASCULAR PROSTHESIS AND A METHOD OF CONNECTING A STRUCTURAL COMPONENT AND A WOVEN GRAFT MATERIAL

(75) Inventors: Alan R. Leewood, Lafayette, IN (US); Blayne A. Roeder, Lafayette, IN (US); Neal E. Fearnot, West Lafayette, IN (US); Jicaho Sun, West Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 1168 days.

(21) Appl. No.: 12/143,230

(22) Filed: Jun. 20, 2008

(65) Prior Publication Data

US 2008/0319530 A1    Dec. 25, 2008

Related U.S. Application Data

(63) Continuation of application No. PCT/US2006/049239, filed on Dec. 22, 2006.

(60) Provisional application No. 60/755,708, filed on Dec. 29, 2005.

(51) Int. Cl.
  *A61F 2/07*  (2013.01)
  *A61F 2/06*  (2013.01)
  *A61F 2/848*  (2013.01)
  *A61F 2/89*  (2013.01)

(52) U.S. Cl.
  CPC .. *A61F 2/07* (2013.01); *A61F 2/89* (2013.01); *A61F 2002/065* (2013.01); *A61F 2002/075* (2013.01); *A61F 2002/8483* (2013.01); *A61F 2002/8486* (2013.01); *A61F 2210/0004* (2013.01); *A61F 2210/0014* (2013.01); *A61F 2220/0058* (2013.01); *A61F 2230/005* (2013.01); *A61F 2230/0054* (2013.01); *A61F 2230/0067* (2013.01); *A61F 2250/0014* (2013.01); *A61F 2250/0017* (2013.01); *A61F 2250/0023* (2013.01)

(58) Field of Classification Search
  USPC ........................................................ 623/1.13
  See application file for complete search history.

(56) References Cited

U.S. PATENT DOCUMENTS

| | | | |
|---|---|---|---|
| 3,479,670 A * | 11/1969 | Medell | 623/1.33 |
| 5,628,788 A | 5/1997 | Pinchuk | 623/1 |
| 6,214,040 B1 * | 4/2001 | Jayaraman | 623/1.13 |
| 6,709,457 B1 * | 3/2004 | Otte et al. | 623/2.4 |
| 6,712,842 B1 * | 3/2004 | Gifford et al. | 623/1.13 |
| 7,118,592 B1 * | 10/2006 | Dang et al. | 623/1.12 |
| 2002/0143384 A1 * | 10/2002 | Ozasa | 623/1.12 |
| 2002/0165601 A1 | 11/2002 | Clerc | 623/1.13 |
| 2006/0276883 A1 * | 12/2006 | Greenberg et al. | 623/1.31 |

FOREIGN PATENT DOCUMENTS

| | | | | |
|---|---|---|---|---|
| WO | WO 98/00090 | 6/1997 | | A61J 2/06 |
| WO | WO 99/32051 | 12/1997 | | A61F 2/06 |
| WO | WO 00/42948 | 1/2000 | | A61F 2/06 |

* cited by examiner

*Primary Examiner* — Yashita Sharma
*Assistant Examiner* — Rebecca Preston
(74) *Attorney, Agent, or Firm* — Brinks Gilson & Lione

(57) ABSTRACT

An endovascular prosthesis that includes a stent and a woven graft material. The stent is connected to the graft material by direct attachment of the stent to the graft material at thermoplastically fused regions of the graft material.

15 Claims, 10 Drawing Sheets

ENDOVASCULAR PROSTHESIS AND A METHOD OF CONNECTING A STRUCTURAL COMPONENT AND A WOVEN GRAFT MATERIAL

RELATED APPLICATIONS

The present document is a continuation of PCT Application Serial No. PCT/US2006/049239, filed Dec. 22, 2006, designating the United States and published in English, which is hereby incorporated by reference in its entirety, and claims priority to U.S. Provisional Application Ser. No. 60/755,708, filed Dec. 29, 2005, which is hereby incorporated by reference in its entirety.

TECHNICAL FIELD

The present invention relates to an endovascular prosthesis and a method of connecting a structural component and a woven graft material, and in particular to attachment of a stent to a graft material.

BACKGROUND

The functional vessels of human and animal bodies, such as blood vessels and ducts, occasionally weaken or even rupture. For example, in the aortic artery the vascular wall can weaken, resulting in dangerous conditions such as aneurysms and dissections. Upon further exposure to hemodynamic forces, such an aneurysm can rupture.

One intervention for weakened, aneurysmal or ruptured vessels is the introduction of an endoluminal device or prosthesis, such as a stent graft, into a patient's vessel. These devices are designed to provide some or all of the functionality of the original, healthy vessel and/or preserve any remaining vascular integrity by reinforcing the portion of the vessel wall that contains the site of vessel weakness or failure. Stent grafts for endoluminal deployment are generally formed from a tube of a biocompatible material and one or more stents to maintain a lumen therethrough. Stent grafts can effectively exclude the aneurysm by sealing both proximally and distally to the aneurysm, such that the patient's blood flow is shunted through the stent graft. A device of this type can, for example, treat various arterial aneurysms, including those in the thoracic aorta, abdominal aorta, iliac, or hypogastric artery.

Two closely related aspects of stent graft function are sealing and fixation. A stent graft typically engages the wall of the lumen on both ends of the aneurysm or other defect, at proximal and distal regions referred to as landing or sealing zones. Typically these sealing zones are located near the termini of the stent grafts. The seal between the stent graft and the vascular wall is typically formed at these locations as a result of the circumferential apposition of the stent graft to the vascular wall, where this apposition is typically maintained by the radial force of the stents that are attached to the stent graft.

It is also desirable to fix, or anchor, the stent graft in place. For some abdominal aortic aneurysm stent grafts, proximal fixation in the neck region of the aorta is critical for long term durability of endoluminal repair. Fixation or anchoring of the stent graft can be achieved using a variety of anchoring mechanisms. One anchoring mechanism relies on the frictional forces that exist between the stent graft and aortic wall due to the radial force supplied by the stent. Fixation may also be achieved by using small hooks or barbs that extend from the stent graft and penetrate the arterial wall. Another method of anchoring the stent graft may involve tissue incapsulation, wherein exposed stent struts and other parts of the stent graft may eventually become completely encapsulated by tissue growth, thereby assisting fixation.

One example of an endoluminal device, is a bifurcated stent graft, which is known for use in treating abdominal aortic aneurysms. The proximal end of the bifurcated stent graft defines a single lumen for placement within the aorta, while the distal end of the bifurcated stent graft defines a bifurcated region that encompasses two lumens for placement in the iliac arteries. One such stent graft is disclosed in PCT application WO98/53761 and is useful for repair of abdominal aortic aneurysms. That application discloses a stent graft that utilizes a biocompatible graft material, such as woven polyester fabric or polytetrafluoroethylene (PTFE), where the graft material is impermeable to blood flow. The stent graft also includes several stents secured therealong. The stent graft is designed to span an aneurysm that extends along the aorta between the iliac and renal arteries. In the WO98/53761 application, the fabric-covered portion of the single-lumen proximal end of the stent graft bears against the wall of the aorta above the aneurysm and distal to the renal arteries to seal off the aneurysm. Thin wire struts of a juxtarenal attachment stent, or anchoring stent, traverse the renal artery ostia without occluding them and barbs on the anchoring stent then help to anchor the stent graft in place.

One example of an endoluminal device, is a bifurcated stent graft, which is known for use in treating abdominal aortic aneurysms. The proximal end of the bifurcated stent graft defines a single lumen for placement within the aorta, while the distal end of the bifurcated stent graft defines a bifurcated region that encompasses two lumens for placement in the iliac arteries. One such stent graft is disclosed in PCT application WO98/53761 and is useful for repair of abdominal aortic aneurysms. That application discloses a stent graft that utilizes a biocompatible graft material, such as woven polyester fabric or polytetrafluoroethylene (PTFE), where the graft material is impermeable to blood flow. The stent graft also includes several stents secured therealong. The scent graft is designed to span an aneurysm that extends along the aorta between the iliac and renal arteries. In the WO98/53761 application, the fabric-covered portion of the single-lumen proximal end of the stent graft bears against the wall of the aorta above the aneurysm and distal to the renal arteries to seal off the aneurysm. Thin wire struts of a juxtarenal attachment stent, or anchoring stent, traverse the renal artery ostia without occluding them and barbs on the anchoring stent then help to anchor the stent graft in place. The stent and the graft material of endoluminal prostheses are often attached using hand-sewn sutures. Unfortunately, this method of attachment is labor-intensive, time-consuming and expensive.

Another method of attaching the stent and the graft material of an endoluminal prosthesis is to cover the stent with an adhesive or a polymer coating that will allow the stent to be bonded to the graft material. Unfortunately, this type of attachment has several drawbacks. For example, these techniques often require multiple steps, since the stent must be treated with the adhesive or polymer coating before the process of attaching the graft can begin. Furthermore, the process of coating the stent with the adhesive or polymer coating usually requires multiple steps. Typically, the adhesive or coating is applied in a first step, using a variety of methods, and then must be cured in a subsequent step. In addition, once the adhesive or polymer coating has been applied to the stent and the graft material has been placed over or within the coated stent, actual bonding between the graft material and the adhesive or the polymer coating usually requires heating the coated stent and the graft material an oven or other heating device. Unfortunately, this heating process limits the types of graft materials that can be used and may also affect the integrity of the graft material itself. In addition, this heating process may also thermoplastically fuse large portions of the graft material.

The present invention seeks to provide an improved endovascular prosthesis and a method of connecting a structural component and a woven graft material.

BRIEF SUMMARY

According to an aspect of the present invention, there is provided an endovascular prosthesis as specified in claim 1.

According to another aspect of the present invention, there is provided a method of connecting material as specified in claim 14.

In one aspect of the invention, there is an endovascular prosthesis that includes at least one structural component and a woven graft material. The structural component is connected to the graft material by direct attachment of the structural component to the graft material at thermoplastically fused regions of the graft material.

The structural component may comprise a stent.

In an embodiment, there is provided a method of connecting a structural component and a woven graft material that comprises providing a woven graft material suitable for forming a lumen and the structural component. The method further comprises directly attaching the structural component to the graft material by thermoplastically fusing the graft material to the structural component to provide at least one thermoplastically-fused region, wherein the at least one thermoplastically fused region occurs substantially where the structural component contacts the graft material.

In another embodiment, there is provided a method of connecting a structural component and a woven graft material, wherein the structural component comprises a stent suitable for supporting a lumen formed by the graft material, wherein the stent comprises at least one stent segment. In this aspect of the invention, the stent may be attached to the graft material by thermoplastically fusing the graft material to at least one stent segment to provide at least one, thermoplastically fused region, wherein the at least one thermoplastically fused region occurs substantially where the at least one stent segment contacts the graft material It is to be understood that the term prosthesis as used herein is intended to encompass all devices to be introduced into a patient whether or not as a prosthetic replacement, such as stent grafts, occlusion devices, filters, and so on.

BRIEF DESCRIPTION OF THE DRAWINGS

Embodiments of the present invention are described below, by way of example only, with reference to the accompanying drawings in which.

DETAILED DESCRIPTION OF THE DRAWINGS AND THE PRESENTLY PREFERRED EMBODIMENTS

Figure 1A:
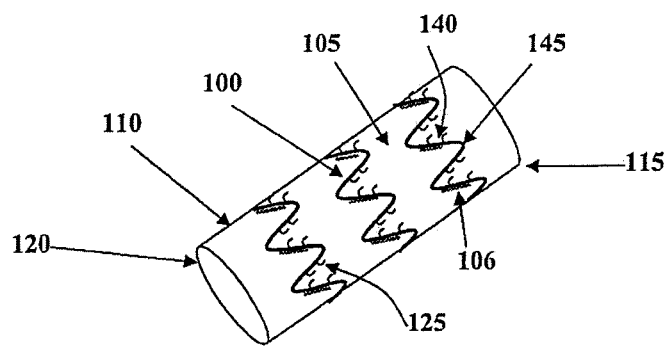
FIGS. 1A, 1B and 1C show a perspective view of a stent graft in which a plurality of stents are directly attached to a woven graft material by way of a suture-free attachment.

The present invention relates to a suture-free endoluminal prosthesis in which the endoluminal prosthesis comprises a stent and a woven graft material. Unlike many endoluminal prostheses, the apparatus disclosed herein does not require sutures for connecting the stent to the graft material. Instead, the graft material of this apparatus possesses a series of thermoplastically fused regions that form direct attachments to the stent. These thermoplastically fused regions can be produced using a variety of techniques. For example, the stent can be heated and then brought into contact with the graft material, causing the graft material that is in contact with the heated stent to melt and form thermoplastically fused regions, and adhere to the stent.

Throughout this specification, when discussing the application of this invention to the aorta, the term distal with respect to a prosthesis is intended to refer to the end of the prosthesis furthest away in the direction of blood flow from the heart, and the term proximal is intended to mean the end of the prosthesis that, when implanted, would be nearest to the heart.

The term "prosthesis" means any replacement for a body part or for a function of that body part; or any device that enhances or adds functionality to a physiological system.

The term "endoluminal" describes objects that are found or can be placed inside a lumen or space in the human or animal body. This includes lumens such as blood vessels, parts of the gastrointestinal tract, ducts such as bile ducts, parts of the respiratory system, etc. "Endoluminal prosthesis" thus describes a prosthesis that can be placed inside one of these lumens.

The term "graft or graft material" means a generally cannular or tubular member which acts as an artificial vessel or prosthesis. A graft by itself or with the addition of other elements, such as structural components, can be an endoluminal prosthesis. The graft comprises a single material, a blend of materials, a weave, a laminate, or a composite of two or more materials.

The term "structural component" means any device that is attached to a prosthesis, such as a stent graft. For example, structural components may comprise stents, radiopaque markers, anchoring, stents, barbs, and lateral support rings for supporting a fenestration. The structural components may be attached to the exterior of the graft, the interior of the graft, and/or may be sandwiched between two or more layers of graft material.

The structural components may be made from numerous base materials, such as: biocompatible metals or other metallic materials; polymers including bioabsorbable or biostable polymers; stainless steels (e.g., 316, 316L or 304); nickel-titanium alloys including shape memory or superelastic types (e.g., nitinol or elastinite); noble metals including platinum, gold or palladium; refractory metals including tantalum, tungsten, molybdenum or rhenium; stainless steels alloyed with noble and/or refractory metals; silver; rhodium; inconel; iridium; niobium; titanium; magnesium; amorphous metals; plastically deformable metals (e.g., tantalum); nickel-based alloys (e.g., including platinum, gold and/or tantalum alloys); iron-based alloys (e.g., including platinum, gold and/or tantalum alloys); cobalt-based alloys (e.g., including platinum, gold and/or tantalum alloys); cobalt-chrome alloys (e.g., elgiloy); cobalt-chromium nickel alloys (e.g., phynox); alloys of cobalt, nickel, chromium and molybdenum (e.g., MP35N or MP20N); cobalt-chromium-vanadium alloys; cobalt-chromium-tungsten alloys; platinum-iridium alloys; platinum tungsten alloys; magnesium alloys; titanium alloys (e.g., TiC, TiN); tantalum alloys (e.g., TaC, TaN); L605; magnetic ferrite; nonmetallic biocompatible materials including polyamides, polyolefins (e.g., polypropylene or polyethylene), nonabsorbable polyesters (e.g., polyethylene terephthalate) or bioabsorb able aliphatic polyesters (eg., homopolymers or copolymers of lactic acid, glycolic acid, lactide, glycolide, para-dioxanone, trimethylene carbonate or epsilon caprolactone); polymeric materials (e.g., poly-L-lactic acid, polycarbonate, polyethylene terephthalate or engineering plastics such as thermotropic liquid crystal polymers (LCPs)); biocompatible polymeric materials (e.g., cellulose acetate, cellulose nitrate, silicone, polyethylene terephthalate, polyurethane, polyamide, polyester, polyorthoester, polyanhydride, polyether sulfone, polycarbonate, polypropylene, high molecular weight polyethylene or polytetrafluoroethylene); degradable or biodegradable polymers, plastics, natural (e.g., animal, plant or microbial) or recombinant material (e.g., polylactic acid, polyglycolic acid, polyanhydride, polycaprolactone, polyhydroxybutyrate valerate, polydepsipeptides, nylon copolymides, conventional poly(amino acid) synthetic polymers, pseudo poly(amino acids) or aliphatic polyesters (e.g., polyglycolic acid (PGA), polylactic acid (PLA), polyalkylene succinates, polyhydroxybutyrate (PHB), polybutylene diglycolate, poly epsilon-caprolactone (PCL), polydihydropyrans, polyphosphazenes, polyorthoesters, polycyanoacrylates, polyanhydrides, polyketals, polyacetals, poly(.alpha.-hydroxyl-esters), poly(carbonates), poly(imino-carbonates), poly(.beta: hydroxy-esters) or polypeptides)); polyethylene terephthalate (e.g., Dacron® or Mylar®); expanded fluoropolymers (e.g., polytetrafluoroethylene (PTFE)); fluorinated ethylene propylene (FEP); copolymers of tetrafluoroethylene (TFE) and per fluoro(propyl vinyl ether) (PFA)); homopolymers of polychlorotrifluoroethylene (PCTFE) and copolymers with TFE; ethylene-chlorotrifluoroethylene (ECTFE); copolymers of ethylene-tetrafluoroethylene (ETFE); polyvinylidene fluoride (PVDF); polyvinyfluoride (PVF); polyaramids (e.g., Kevlar®); polyfluorocarbons including polytetrafluoroethylene with and without copolymerized hexafluoropropylene (e.g., Teflon® or Goretex®); expanded fluorocarbon polymers; polyglycolides; polyiactides; polyglycerol sebacate; polyethylene oxide; polybutylene terepthalate; polydioxanones; proteoglycans; glycosaminoglycans; poly(alkylene oxalates); polyalkanotes; polyamides; polyaspartimic acid; polyglutarunic acid polymer; poly-p-diaxanone (e.g., PDS); polyphosphazene; polyurethane including porous or nonporous polyurethanes; poly (glycolide-t(methylene carbonate); terpolymer (copolymers of glycolide, lactide or dimethyltrimethylene carbonate); polyhydroxyalkanoates (PHA); polyhydroxybutyrate (PHB) or poly(hydroxybutyrate-co-valerate) (PHB-co-HV); poly (epsilon-caprolactone) (e.g., lactide or glycolide); poly(epsilon-caprolactonedimethyltrimethylene carbonate); polyglycolic acid (PGA); poly-L and poly-D(lactic acid) (e.g., calcium phosphate glass); lactic acid/ethylene glycol copolymers; polyarylates (L-tyrosine-derived) or free acid polyarylates; polycarbonates (tyrosine or L-tyrosine-derived); poly(ester-amides); polypropylene fumarate-co-ethylene glycol) copolymer (e.g., fumarate anhydrides); polyanhydride esters; polyanhydrides; polyorthoesters; prolastin or silk-elastin polymers (SELP); calcium phosphate (bioglass); compositions of PLA, PCL, PGA ester; polyphosphazenes; polyamino acids; polysaccharides; polyhydroxyalkanoate polymers; various plastic materials; Teflon®; nylon; block polymers or copolymers; Leica RM2165; Leica RM2155; organic fabrics; biologic agents (e.g., protein, extracellular matrix component, collagen, fibrin); small intestinal submucosa (SIS) (e.g., vacuum formed SIS); collagen or collagen matrices with growth modulators; aliginate; cellulose and ester; dextran; elastin; fibrin; gelatin; hyaluronic acid; hydroxyapatite; polypeptides; proteins; ceramics (e.g., silicon nitride, silicon carbide, zirconia or alumina); bioactive silica-based materials; carbon or carbon fiber; cotton; silk; spider silk; chitin; chitosan (NOCC or NOOC-G); urethanes; glass; silica; sapphire; composites; any mixture, blend, alloy, copolymer or combination of any of these; or various other materials not limited by these examples.

The term "stent" means any device that provides rigidity, expansion force or support to a prosthesis, such as a stent graft. In one configuration, the stent may represent a plurality of discontinuous devices. In another configuration, the stent may represent one device. Stents may have a wide variety of configurations and may be balloon-expandable or self-expanding. Typically, stents have a circular cross-section when fully expanded, so as to conform to the generally circular cross-section of a body lumen. In one example, a stent may comprise struts and acute bends or apices that are arranged in a zig-zag configuration in which the struts are set at angles to each other and are connected by the acute bends.

A variety of biocompatible materials may be employed to construct the stent, or portions of the stent, including metals and/or alloys, medically-acceptable polymers and/or bioabsorbable polymers or materials. The metals and/or alloys may, among other things, include stainless steel, tantalum, -nitinol, gold, silver, tungsten, platinum, inconel, cobalt-chromium alloys and iridium, all of which are commercially available metals or alloys used in the fabrication of medical devices. In a preferred configuration, the stent is constructed from nitinol, stainless steel and/or cobalt-chromium alloys.

The term "partial stent" means a stent that does not form a complete tubular shape, and is typically configured as a stent that has been divided along its axis or parallel to its axis.

The term "stent graft" means a stent that has been connected to a graft. A stent can be connected the interior of the graft, the exterior of the graft, and/or sandwiched between two layers of graft material. A stent can also be secured to one of the openings of the graft such that the stent extends from the graft.

"Biocompatible" describes something that can be substantially non-toxic in the in vivo environment of its intended use, and is not substantially rejected by the patient's physiological system (i.e., is nonantigenic). This can be gauged by the ability of a material to pass the biocompatibility tests set forth in International Standards Organization (ISO) Standard No. 10993 and/or the U.S. Pharmacopeia (USP) 23 and/or the U.S. Food and Drug Administration (FDA) blue book memorandum No. G95-1, entitled "Use of International Standard ISO-10993, Biological Evaluation of Medical Devices Part-1: Evaluation and Testing." Typically, these tests measure a material's toxicity, infectivity, pyrogenicity, irritation potential, reactivity, hemolytic activity, carcinogenicity, and/or immunogenicity. A biocompatible structure or material, when introduced into a majority of patients, will not cause a significantly adverse reaction or response. Furthermore, biocompatibility can be affected by other contaminants such as prions, surfactants, oligonucleotides, and other agents or contaminants.

As used herein, "thermoplastically fused region or regions" means a melted region of graft material that has lost some or all of its woven attributes, wherein a portion of each thermoplastically fused-region is directly adhered or attached to a portion of the stent. The thermoplastically fused region(s) of the graft material should not comprise anymore of the graft material than is required to form the attachment between the stent and the graft material. Furthermore, the thermoplastically fused region(s) may comprise a variety of shapes. For example, the thermoplastically fused region(s) may be one or more points or lines. The thermoplastically fused region may comprise 30% or less of the graft material. Preferably, the thermoplastically fused region will comprise 20% or less of the graft material. Preferably, the thermoplastically fused region will comprise 15% or less of the graft material. More preferably, the thermoplastically fused region may comprise 10% or less of the graft material. More preferably, the thermoplastically fused region may comprise 5% or less of the graft material.

Figure 1B:
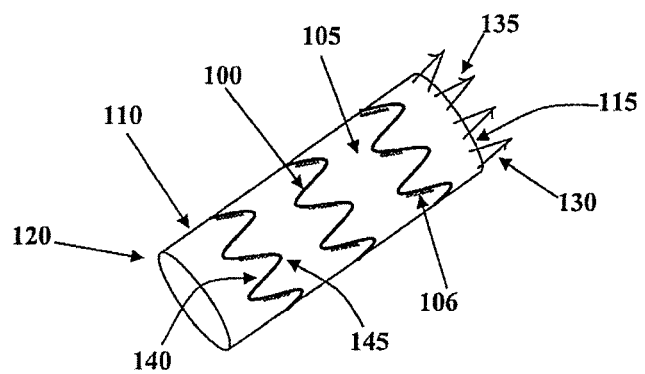
Figure 1C:
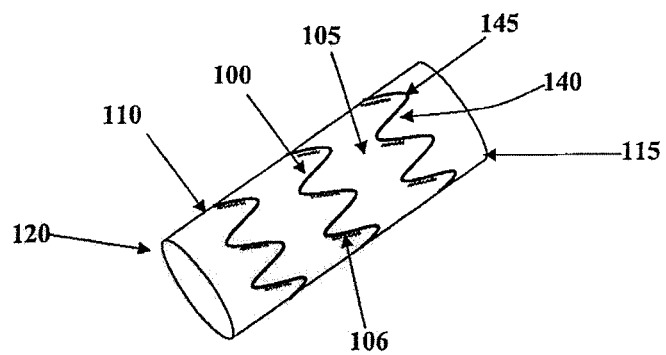

FIGS. 1A, 1B and 1C show a stent graft 110, in which a plurality of stents 100 are directly attached to a woven graft material 105 by way of a suture-free attachment. Unlike other methods of attaching a stent and a graft material, the formation of the suture-free attachment, described herein, does not require heating the entire stent and graft material. Instead, formation of the suture free attachment, as described herein, only heats the woven graft material at selected locations where the stent contacts the graft material, forming a plurality of thermoplastically fused or melted regions 106. In this embodiment, the graft material 105 is connected directly to the stents 100 by the plurality of thermoplastically fused or melted regions 106.

The attachment of the stents 100 and the woven graft material 105 provides the stent graft 110, which extends between a stent graft proximal end 115 and a stent graft distal end 120. The stents 100 is made from a base material. Preferably, the base material that forms the stents 100 is a metal, such as stainless steel; a shape memory alloy, such as nitinol; or another biocompatible alloys. More preferably, the base material that forms the stents 100 is a stainless steel.

In one embodiment, the stent graft 110 may be equipped with a plurality of barbs 125 to secure the stent graft 110 to the vessel wall of a patient (See FIG. 1A). In another embodiment, the stent graft 110 maybe equipped with a plurality of anchoring stents 130 and a plurality of anchoring stent barbs 135 to secure the prosthesis to the vessel wall of the patient (See FIG. 1B). In a further embodiment, the stent graft 110 may rely solely on the radial force of the stents 100, which create an interference fit with the vessel wall of the patient, to secure the stent graft 110 within the patient's vessel (See FIG. 1C).

Each of the stents 100 may be converted between a compressed state and an expanded state. In addition, the stents 100 may be balloon-expandable or self-expanding. Preferably, the stent 100 is self-expanding. The stent 100 may have a generally circular cross-section when fully expanded, so as to conform to the generally circular cross-section of a body lumen. Additionally, the stent 100 may be assembled in a variety of different configurations. For example, the stent 100 may be composed of a variety of components, such as a plurality of struts 140 and a plurality of acute bends 145. In one embodiment, these components may be arranged in a zig-zag configuration in which the plurality of struts 140 are set at angles to each other and are connected by the plurality of acute bends 145. The struts 140 may thus be connected into an endless loop, forming a generally tubular structure.

The graft material 105 is a biocompatible material that is both flexible and abrasion resistant. Furthermore, the graft material 105 should be selected from those materials that are particularly well suited for thermoplastic deformation, such that the material can be thermoplastically fused to a stent 100. Preferably, the woven graft material 105 is a woven polyester. More preferably, the woven graft material 105 is a polyethylene terephthalate (PET), such as DACRON® (DUPONT, Wilmington, Del.) or TWILL WEAVE MICREL (VASCUTEK, Renfrewshire, Scotland). Woven polyesters, such as Dacron, possess varying degrees of porosity, where the degree of porosity can be selectively controlled based on the weaving or knitting process that is used to produce the woven polyester. Consequently, depending on the application, the porosity can be adjusted to encourage incorporation of a patient's tissue into the woven graft material, which in turn may more securely anchor the prosthesis within the patient's vessel or lumen. Furthermore, the degree of porosity can also be adjusted to provide a woven graft material that is impermeable to liquids, including blood or other physiological fluids.

In another embodiment, the woven graft material 105 may be made of a single material, or it may be a blend, weave, laminate, or composite of two or more materials. The graft material 105 may also include other additives, such as plasticizers, compatibilizers, surface modifiers, biological materials such as peptides and enzymes, and therapeutic agents such as drugs or other medicaments.

The stent 100 and the graft material 105 may be connected by melting portions of the graft material 105 to provide the plurality of thermoplastically fused regions 106, such that the melted or thermoplastically fused regions 106 form direct attachments to the stent 105 at selected locations. In another embodiment, the thermoplastically fused regions 106 may be attached to substantially the entire stent 105. A variety of techniques may be employed to produce the thermoplastically fused regions 106. In one embodiment, the stent 100, or portions of the stent 100, can be heated and while hot brought into contact with the graft material 105, such that at least a portion of the graft material melts, to provide the thermoplastically fused regions; and adheres to the stent 100. In another embodiment, the stent 100 maybe brought into contact with the graft material 105 and then the stent 100 may be heated, such that at least a portion of the graft material 105 melts and adheres to the stent 100. In a further embodiment, the graft material 105 may be heated substantially at the locations where the graft material 105 contacts the stent 100. In either case, the thermoplastically fused regions are located substantially at selected locations where the graft material 105 contacts the stent 100 (See FIGS. 2A-2D). A variety of methods may be used to heat the stent 100. One method of heating the stent 100 involves passing an electric current through the stent 100 or a segment of the stent 100 (See FIG. 3A and FIG. 3B). Other methods of heating the stent 100 or causing thermoplastic deformation of the graft material 105 include ultrasonic welding, high frequency welding, electromagnetic welding, hot gas welding, and microwave welding.

In one embodiment, the stents 100 may be attached to the exterior of the graft material 105. In another embodiment, the stents 100 may be attached to the interior of the graft material 105. In a further embodiment, the stents 100 may be sandwiched between two layers of graft material 105 (not shown).

Attaching the stent 100 and the graft material 105 by melting a portion of the graft material 105 may provide a more efficient bonding technique, since this attachment technique may reduce the time and expense that are associated with using sutures. In addition, this attachment technique may provide a flexible and continuous attachment between the stent 100 and the graft material 105. Other beneficial aspects of this attachment technique include the fact that formation of the connection between the stent 100 and the graft material 105 does not require heating or baking of the entire assembled stent graft 110, which may negatively impact the integrity and durability of the graft material 105. Furthermore, this technique does not require that the stent 100 be coated or treated with adhesives or coatings, instead the stent 100 is directly attached to the graft material 105 byway of the melted or thermoplastically fused regions 106. This type of attachment is also compatible with woven graft materials, such as Dacron®.

FIGS. 2A, 2B, 2C, 2D and 2E show a cross-sectional view of a stent section 111 and a portion of woven graft material 116, wherein the stent section 111 is connected to the portion of graft material 116 by direct attachment between the stent section 111 and the portion of graft material 116 at a thermoplasitcally fused region 121 of the graft material 116. In this embodiment, the surface of the stent section 111 is defined by a contacting face 126, an opposing face 131, first edge 136, and a second edge 137, while the graft material 116 comprises a first surface 141, a second surface 146 and an interior region 150 extending therebetween. Furthermore, the length of thermoplastically fused region 121 is defined by a width 155.

Figure 2A:
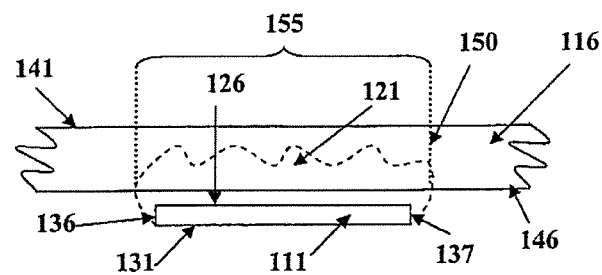
FIGS. 2A, 2B, 2C, 2D and 2E show across-sectional view of a stent section and a portion of woven graft material, wherein the stent section is connected to the portion of woven graft material by direct attachment between the stent section and the graft material at a thermoplastically fused region of the graft material.

In FIG. 2A the contacting face 126 and the edges 136 and 137 of the stent section 111 are substantially enclosed by the thermoplastically fused region 121, thus directly connecting the stent section 111 and the graft material 116. In this embodiment, the fused region 121 extends into the interior region 150, but does not extend to the first surface 141 and the width 155 is substantially equivalent to the distance between the first edge 136 and the second edge 137. Furthermore, the thermoplastically fused region 121 may be substantially adhered to the contacting face 126 and the first and second edges, 136 and 137, respectively.

Figure 2B:
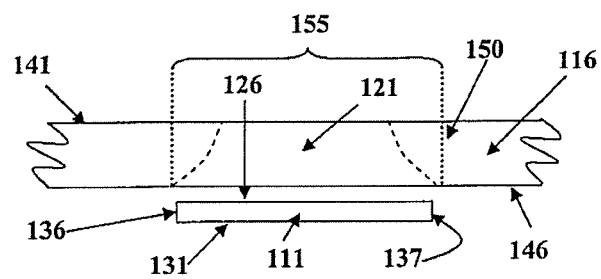

In FIG. 2B the contacting face 126 and the edges 136 and 137 of the stent section 111 are substantially enclosed by the thermoplastically fused region 121, thus directly connecting the stent section 111 and the graft material 116. In this embodiment, the fused region 121 extends through the entire interior region 150 and the width 155 is substantially equivalent to the distance between the first edge 136 and the second edge 137. Furthermore, the thermoplastically fused region 121 may be substantially adhered to the contacting face 126 and the first and second edges, 136 and 137, respectively.

Figure 2C:
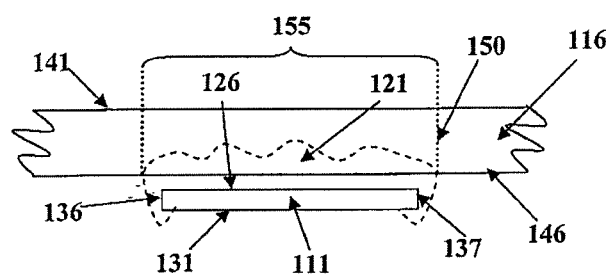

In FIG. 2C the contacting face 126 and the edges 136 and 137 of the stent section 111 are substantially enclosed by the thermoplastically fused region 121, while portions of the opposing face 131 are also enclosed by the thermoplastically fused region 121, thus directly connecting the stent section 111 and the graft material 116. In this embodiment, the fused region 121 extends into the interior region 150, but does not extend to the first surface 141 and the width 155 is substantially equivalent to the distance between the first edge 136 and the second edge 137.

Figure 2D:
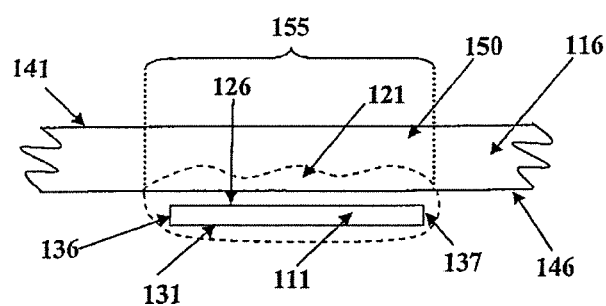

In FIG. 2D the contacting face 126, the edges 136 and 137, and the opposing face 131 of the stent section 111 are substantially enclosed by the thermoplastically fused region 121, thus directly connecting the stent section 111 and the graft material 116. In this embodiment, the fused region 121 extends into the interior region 150, but does not extend to the first surface 141. In this, embodiment, the width 155 is substantially equivalent to the distance between the first edge 136 and the second edge 137.

Figure 2E:
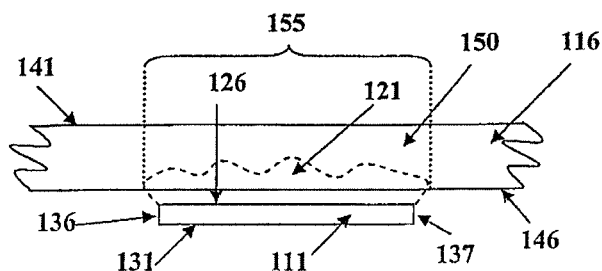

In FIG. 2E the contacting face 126 and the edges 136 and 137 of the stent section 111 are substantially enclosed by the thermoplastically fused region 121, thus directly connecting the stent section 111 and the graft material 116. In this embodiment, the fused region 121 extends into the interior region 150, but does not extend to the first surface 141 and the width 155 is substantially equivalent to the distance between the first edge 136 and the second edge 137. Furthermore, the thermoplastically fused region 121 may be substantially adhered to the contacting face 126.

The various embodiments provided in FIGS. 2A, 2B, 2C, 2D and 2E, and combinations of these embodiment, may be selectively obtained based on a variety of factors including the identity of the woven graft material 116, the porosity of the woven graft material 116, the physical properties of the woven graft material 116, the thickness of the woven graft material 116, the dimensions of the stent section 1,11, the physical properties of the stent section 111, the pressure with which the stent section 111 contacts the graft material 116 while the stent section 111 is being heated, the temperature to which the stent section 111 is heated and the amount of time the stent section 111 is heated, to name a few. In addition, the embodiments illustrated in FIGS. 2A, 2B, 2C, 2D and 2E may exist as combinations. Furthermore, any number of the embodiments illustrated in FIGS. 2A, 2B, 2C, 2D and 2E may be present in the same stent graft 10.

Figure 3A:
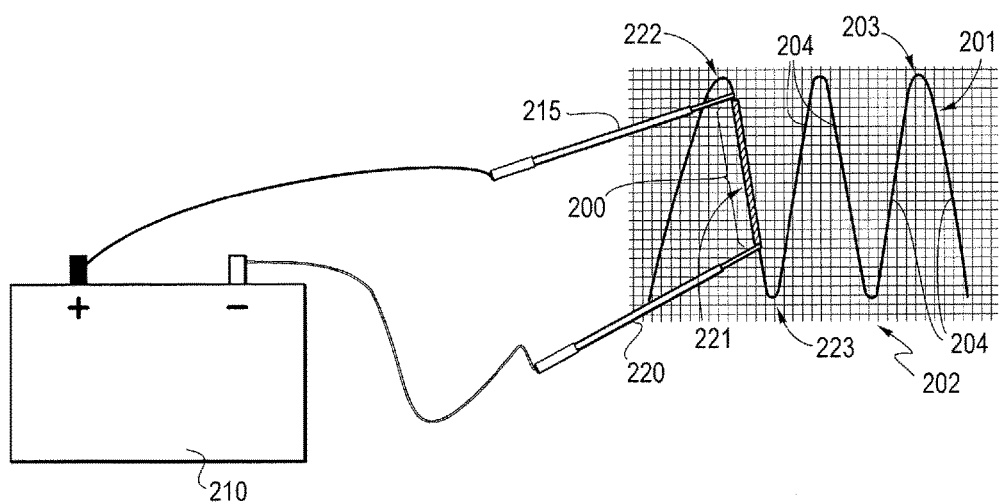
FIG. 3A shows a schematic view of a battery, a positive electrode, and a negative electrode for thermoplastically fusing a stent segment and a woven graft material.

FIG. 3A shows a schematic view of a battery 210, a positive electrode 215, and a negative electrode 220 for thermoplastically fusing a stent segment 200 and a woven graft material 202 to provide a thermoplastically fused region 221. In order to simplify this illustration, FIG. 3A only shows a portion of a stent 201. The portion of the stent 201 depicted in FIG. 3A comprises a plurality of acute bends 203 that are connected by a plurality of struts 204. In FIG. 3A the portion of the stent 201 is shown with five acute bends 203 and six struts 204. In this embodiment, the battery 210, the positive electrode 215 and the negative electrode 220 are being employed to heat the stent segment 200 by passing an electric current through the stent segment 200. The stent segment 200 is defined as the length of stent 201 that extends between the point where the positive electrode 215 contacts the stent 201 and the point where the negative electrode 220 contacts the stent 201. In this embodiment, the electrodes 215 and 220 contact the stent 201 near a first acute bend 222 and near an adjacent second acute bend 223, such that the electrodes 215 and 220 define the stent segment 200 therebetween. In this example, the stent segment 200 happens to be an individual stent strut 203, however the stent segment 200 can include any portion of the stent 201 or the entire stent 201 (See FIG. 3B). For example, in one embodiment, the stent segment may comprise an acute bend 223 and the thermoplastically fused region 221 will directly attach the stent 201 and the graft material 202 at the selected acute bend 223.

In this configuration, heating the stent segment 200 with the positive electrode 215 and the negative electrode 220 produces the thermoplastically fused region 221, which should substantially correspond to the stent segment 200 (See FIGS. 2A-2D). In this embodiment, the stent segment 200 is being heated while in contact with the graft material 202, however the stent segment 200 could also be heated, by a variety of other heating methods, apart from the graft material 202 and then once at the desired temperature could be brought into contact with the graft material 202. With regard to heating the stent segment 200, the stent base material may be selected based on its ability to be heated to a temperature equal to or above the temperature at which the woven graft material 202 thermoplastically deforms.

In one embodiment, the stent 201 is attached to the graft material 202 by sequentially heating one stent segment 200 at a time, until a desired plurality of stent segments 200 are attached to the graft material 202 via a plurality of thermoplastically fused regions 221. In another embodiment, the stent 201 is attached to the graft material 202 by heating the entire stent 201 at once (See FIG. 3B).

Figure 3B:
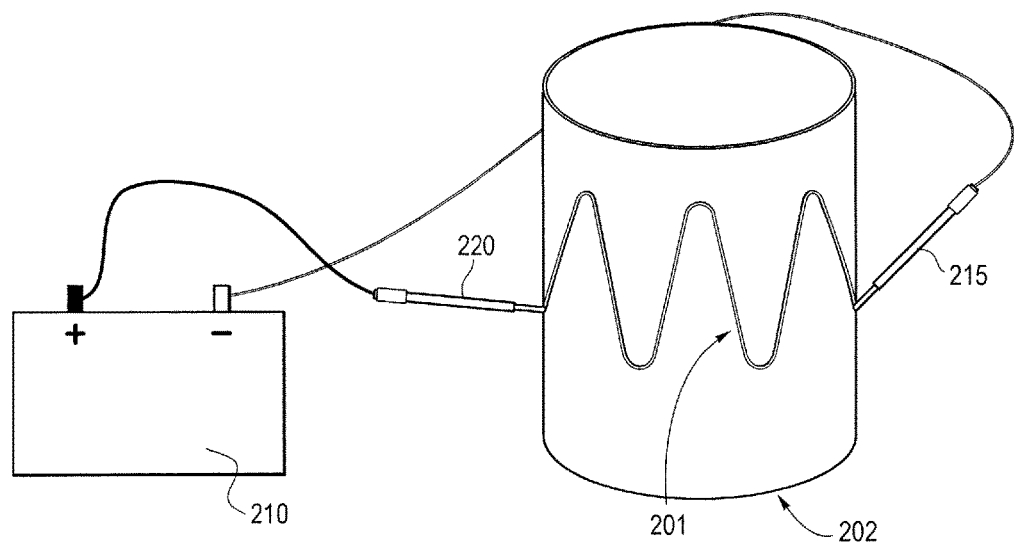
FIG. 3B shows a schematic view of a battery, a positive electrode, and a negative electrode for thermoplastically fusing a stent and a woven graft material.

FIG. 3B shows a schematic view of a battery, a positive electrode 215 and a negative electrode 220 for thermoplastically fusing a stent 201 and a woven graft material 202. In this embodiment, the stent 201 is thermoplastically fused to the woven graft material 202 by passing an electric current through the entire stent 201. In this embodiment, the stent 201 is positioned over the exterior of the graft material 202 and the entire stent is heated by selectively placing the electrodes 215 and 220 such that an electric current will pass through the entire stent 201. Thus, in this embodiment, the stent segment 200 is the entire stent 201.

The duration of the heating process and the amount of current employed will depend on a variety of factors, including the conductive properties of the stent 200, the dimensions of the stent 201 or stent segment 200, the dimensions of the graft material 202, the physical properties of the graft material 202, and/or the melting point of the graft material 202. Although FIG. 3A and FIG. 3B both show the use of two electrodes 215 and 220, as well as one battery 210, in some circumstances it may be necessary to employ additional electrodes and/or batteries (not shown). For example, when attempting to heat a large stent, it may be more difficult to maintain or achieve the desired temperature across the entire area to be heated. Thus it may be necessary to use additional electrodes and/or batteries to maintain or achieve the desired temperature.

In one embodiment, it may be desirable to attach the stent 201 and the graft material 202 by forming a plurality of suture free attachments between each of the struts 204 and the graft material 202. In another embodiment, it may be desirable to attach the stent 201 and the graft material 202 by forming a plurality of suture free attachments between the bends 203 and the graft material 202. In a further embodiment, it may be desirable to attach the stent 201 and the graft material 202 by forming one suture free attachment between the entire stent 201 and the graft material 202.

The process of heating the stent 201, or the stent segment 200, should heat the stent 201, or the stent segment 200, to an extent that is sufficient to melt, or thermoplastically fuse, an amount of the graft material 202 when the heated stent 201, or stent segment 200, is brought into contact with the graft material 202. The amount of graft material 202 that is thermoplastically fused should be sufficient to form an attachment between the stent 201, or stent segment 200, and the graft material 202. However, this process should not affect the integrity of the graft material 202. Thus, the heated stent segment 200, or the stent 201, should not burn the graft material 200 or cause holes to be formed in the graft material 200. In addition, the heated stent segment 200, or the stent 201, should not substantially weaken the graft material.

In a preferred embodiment the graft material 202 is Dacron® and the stent 201 or stent segment 200 is heated to a temperature of about 250° C. to 300° C. In one embodiment, the graft material 202 is attached to the exterior of the stent 201. In a further embodiment, the graft material 202 is attached to the interior of the stent 201. In an additional embodiment, the stent 201 is sandwiched between two pieces of graft material 202, such that one piece of graft material 200 is attached to the exterior of the stent 201 and another piece of graft material 202 is attached to the interior of the stent 201 (not shown).

Although a variety of techniques can be used to heat the stent 201 or the stent segment 200, the embodiments shown in FIGS. 3A and 3B employ an electric current. As a result, the stent segment 200 and the stent 201 shown in FIGS. 3A and 3B must be capable of conducting an electric current.

Figure 3C:
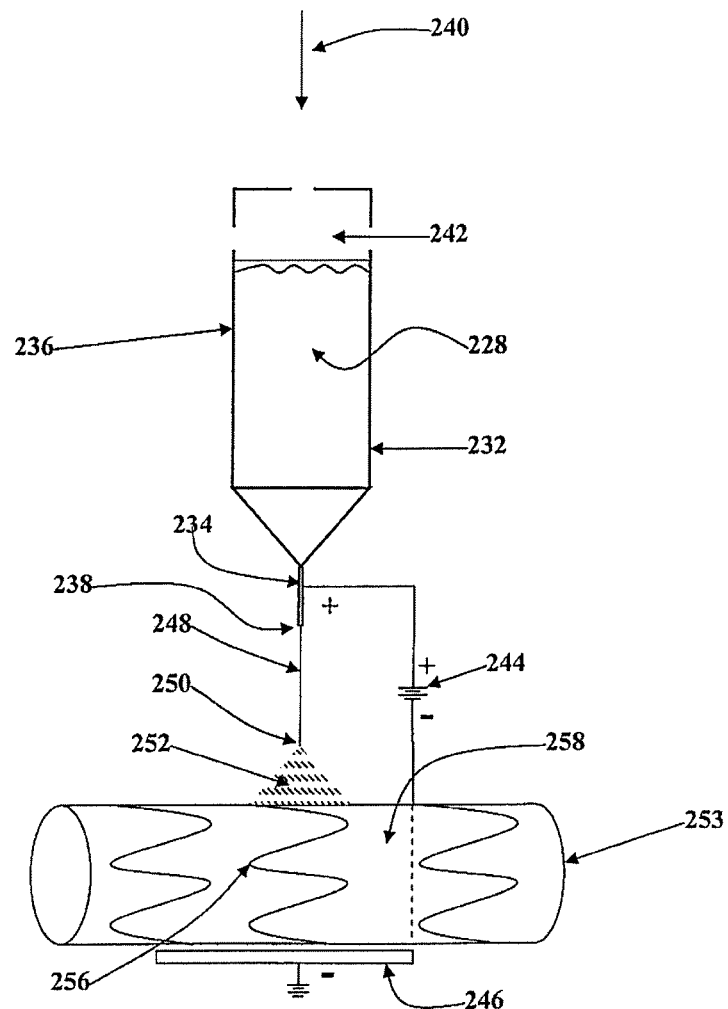
FIG. 3C shows a schematic view of an electrospinning device for creating thermoplastically fused regions to directly attach a stent and a woven graft.

FIG. 3C shows a schematic view of an electrospinning device for creating thermoplastically fused regions to directly attach a stent 256 and a woven graft 258. The basic electrospinning components shown in FIG. 3C and a detailed discussion of electrospinning is disclosed in U.S. Patent Application Publication Ser. No. 2004/0051201 filed Dec. 2, 2002, which is incorporated by reference in its entirety herein.

In this embodiment, a liquid polymer 228 maybe generated by either heating the polymer until it achieves a plastic state or mixing the polymer with a solvent to form a solution. The liquid polymer 228 may be loaded into a syringe-like container 232 that is fluidly connected to a blunt needle 234 to form a spinneret 236. The needle 234 may have a distal opening 238 through which the liquid polymer 228 may be ejected by a controlled force 240, represented here in a simplified manner as being supplied by a plunger 242, but can be any appropriate controllable variable rate fluid displacement system and should be automated to ensure accurate flow rates.

A significant electric potential 244 may be established between the spinneret 236 and a receiving plate 246. The electric potential 244 aids the force 240 in motivating the liquid polymer 228 and by reducing the surface tension of the displaced liquid polymer 228 as it travels from the spinneret 236 toward the receiving plate 246. The combined action of the electric potential 244 and the displacement force 240 creates a jet of polymer 248 that, due to the charge, splays at a position 250 between the spinneret 236 and the receiving plate 246. The splaying action creates a plurality of tiny threads or fibrils 252 that may be adhered on selected locations of the stent graft 253, which is located between the spinneret 236 and the receiving plate 246. When the liquid polymer 228 comprises the solution, the threads or fibrils 252 may or may not be dry upon reaching the stent graft 253, depending on a number of factors, including the volatility of the solvent, the physical characteristics of the polymer and the environment in which the process is being carried out. When the liquid polymer 228 comprises the plastic state, the threads or fibrils 252 may or may not be in a partially plastic state upon reaching the stent graft 253, depending on a variety of factors, including the environment in which the process is being carried out and the physical characteristics of the polymer.

In one embodiment, the threads or fibrils 252 resulting from the electrospinning process may be directed at selected segments of the stent graft 253, such that the threads contact the stent 256 and a portion of the underlying woven graft 258. The threads or fibrils 252 may then adhere to the to both the stent 256 and the underlying woven graft material 258, thus forming a direct attachment between the stent 256 and the graft 258. In a preferred embodiment, the threads or fibrils 252 will contact the graft 258 while still hot enough to thermoplastically fuse a portion of the graft 258, thus forming a secure bond between the threads or fibrils 252 and the graft 258. In order to achieve thermoplastic deformation when the threads or fibrils 252 contact the graft 258 it may be necessary to carry out the electrospinning process in an environment with an elevated temperature and/or to increase the temperature of the graft 258. Increasing the temperature of the environment and the graft 258 may also ensure that the threads or fibrils 252 do not crystallize when they contact the graft 258. In another embodiment, the temperature of the scent 256 may be elevated to ensure that a portion of the threads or fibrils 252 melt onto the stent 256, which may create a more secure attachment between the stent 256 and the threads or fibrils 252.

In another preferred embodiment, the threads or fibrils 252 will contact the graft 258 while still containing enough solvent to thermoplastically fuse, or melt, a portion of the graft 258, thus forming a secure bond between the threads or fibrils 252 and the graft 258.

In a preferred embodiment, the liquid polymer 228 is selected such that it is the same as the polymer forming the graft 258. In a more preferred embodiment, the liquid polymer 228 is PET and the graft 258 is DACRON®.

Figure 4:
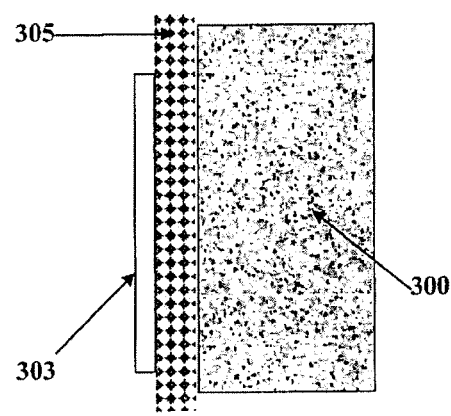
FIG. 4 shows a cross-sectional view of a heat sink, a stent section, and a portion of graft material, where the heat sink is employed for formation of a suture-free attachment between the stent section and the portion of woven graft material.

FIG. 4 shows a cross-sectional view of a heat sink 300, a stent section 303, and a portion of woven graft material 305, where the heat sink 300 is employed for formation of a suture-free attachment between the stent section 303 and the portion of woven graft material 305. The heat sink 300 may allow the graft material 305 that is directly contacting the stent 303 to melt, but may dissipate the heat such that the graft material 305 does not burn or melt all the way through. In one embodiment, the heat sink 300, which may consist of a thermally conductive metal, is located such that it is in contact with and adjacent to the graft material 305 and is on the opposite side of the graft material 305 from the stent 303.

Figure 5:
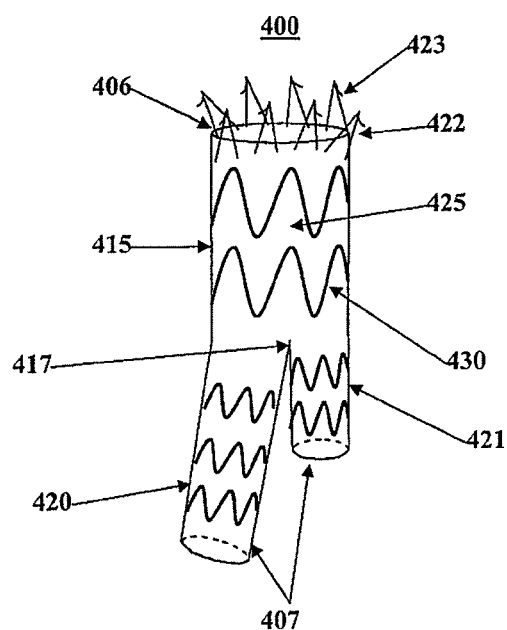
FIG. 5 shows a perspective view of a suture-free bifurcated stent graft.

FIG. 5 shows a perspective view of a suture-free bifurcated stent graft 400. The stent graft 400 extends between a bifurcated proximal end 406 and two bifurcated distal ends 407. The stent graft 400 consists of a body 415, a longer leg 420, and a shorter leg 421. Both legs 420 and 421 are attached to the body 415 at a bifurcation 417. The body 415 and the legs 420 and 421 are composed of a graft material 425 and a plurality of stents 430. Although the stents 430 may be balloon expandable or self-expanding, in a preferred embodiment, the stents 430 are self-expanding. In addition, the stent graft 400 may also include a plurality of proximal anchoring stents 422 and barbs 423 that are located near the proximal end 406, where the anchoring stents 422 are attached to and extend proximally from the graft material 425. In a preferred embodiment, the anchoring stents 422 are delivered in a compressed state and are self-expanding. In this embodiment, the stents 430 are directly attached to the graft material 425 by thermoplastically fused regions of the exterior of the graft material 425.

Figure 6:
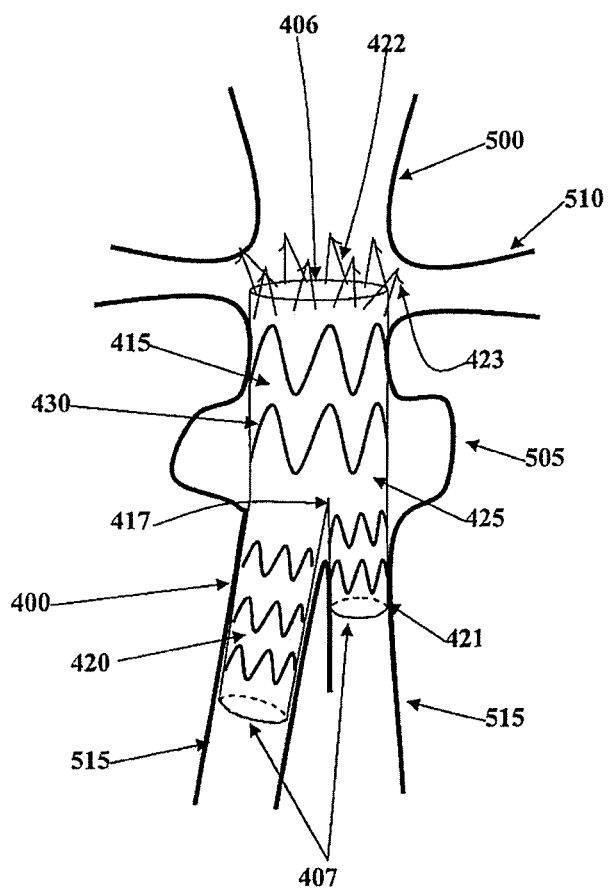
FIG. 6 shows a perspective view of a suture-free bifurcated stent graft and a cross-sectional view of an abdominal aorta with an abdominal aortic aneurysm (AAA), where the preferred device is implanted within the abdominal aorta.

FIG. 6 shows a perspective view of a suture-free bifurcated stent graft 400 and a cross-sectional view of an abdominal aorta 500 with an abdominal aortic aneurysm (AAA) 505, where the preferred device is implanted within the abdominal aorta 500.

As previously discussed in FIG. 4, the stent graft 400 extends between the proximal end 406 and the two distal ends 407 and includes the body 415, the longer leg 420, and the shorter leg 421, where the legs 420 and 421 are attached to the body 415 at the bifurcation 417.

In this embodiment, the proximal end 406 of the stent graft 400 is secured within the aorta 500 by the radial force of the stents 430 and by attaching the anchoring stents 422, by way of the barbs 423, to the aorta 500. The stent graft 400 will preferably achieve blood-tight seals at the proximal end 406 and the distal ends 407, so that blood flow will be directed through the stent graft, thus excluding the aneurysm 505 and reducing the hemodynamic pressure within the aneurysm 505. In this embodiment, the proximal end 406 of the stent graft 400 contacts the vascular tissue of the aorta 500 below the renal arteries 510, while the leg modules 420 and 421 extend into the iliac arteries 515 such that the distal ends 407 contact the vascular tissue of the iliac arteries 515. The distal ends 407 are secured within the iliac arteries 515 by the radial force of the stents 430. In this embodiment, the proximal end 406 preferably forms a seal at or near the renal arteries 450, while the distal ends 407 of each of the leg modules 420 and 421 preferably form seals within the iliac arteries 515.

Figure 7:
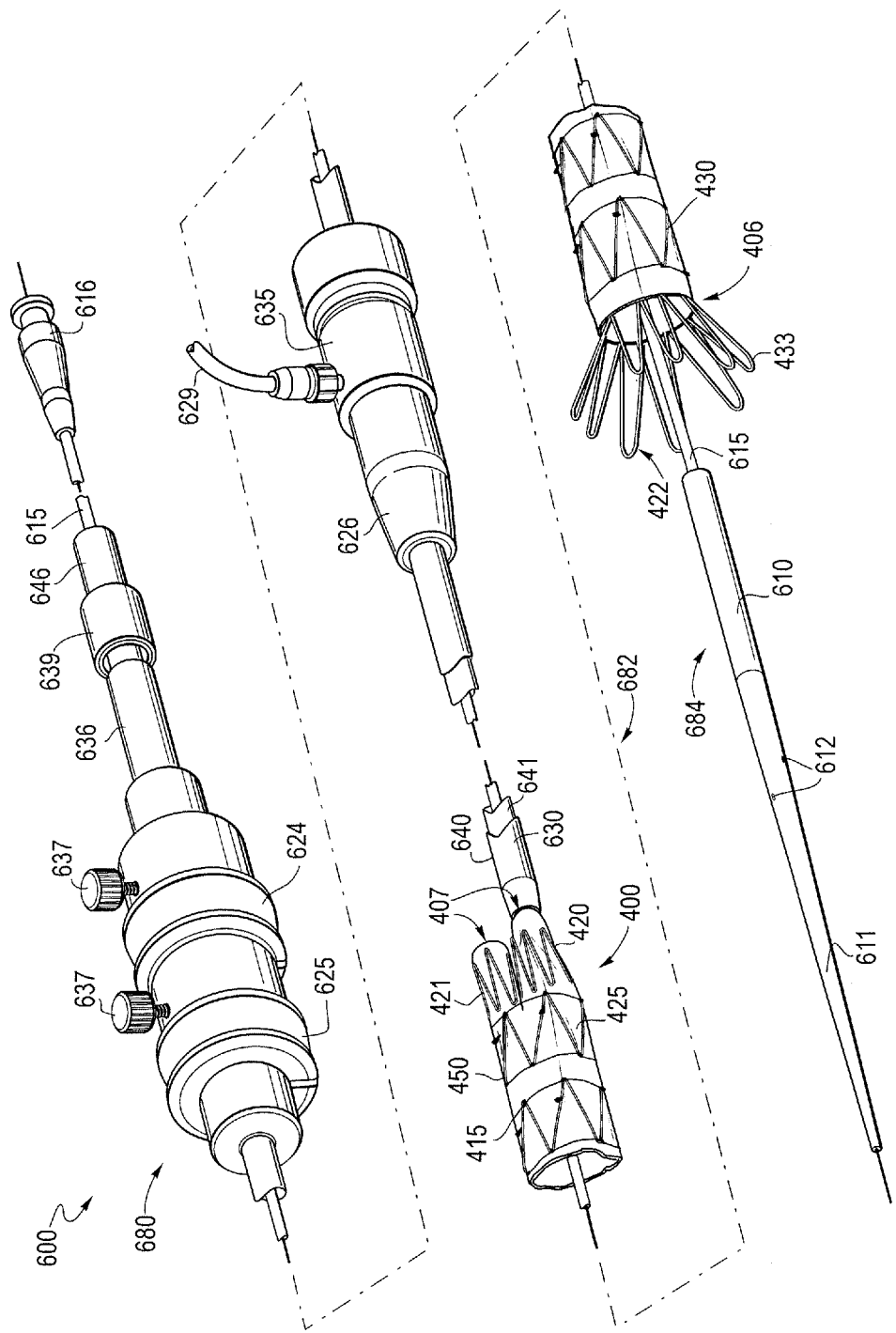
FIG. 7 shows a perspective view of a suture-free bifurcated stent graft in combination with an endovascular deployment system or introducer.

FIG. 7 shows a perspective view of a suture-free bifurcated stent graft 400 in combination with an endovascular deployment system or introducer 600. Although a variety of delivery techniques and apparatuses may be employed to deploy the suture-free bifurcated stent graft 400, in a preferred embodiment the introducer 600 is employed. The introducer 600 is described in greater detail in PCT application WO98/53761.

The introducer 600 includes an external manipulation section 680, a distal attachment region 682 and a proximal attachment region 684. The distal attachment region 682 and the proximal attachment region 684 secure the distal ends 407 and the proximal end 406, respectively. During the medical procedure to deploy the stent graft 400, the distal and proximal attachment regions 682 and 684 will travel through the lumen to a desired deployment site. The external manipulation section 680, which is acted upon by a user to manipulate the introducer, remains outside of the patient throughout the procedure.

The proximal attachment region 684 of the introducer 600 includes a cylindrical sleeve 610. The cylindrical sleeve 610 has along tapered flexible extension 611 extending from its proximal end. The flexible extension 611 has an internal longitudinal aperture (not shown). This longitudinal aperture facilitates advancement of the tapered flexible extension 611 along an insertion wire (not shown). The longitudinal aperture also provides a channel for the introduction of medical reagents. For example, it may be desirable to supply a contrast agent to allow angiography to be performed during placement and deployment phases of the medical procedure.

A thin-walled metal tube 615 is fastened to the extension 611. The thin-walled metal tube 615 is flexible so that the introducer. 600 can be advanced-along a relatively tortuous vessel, such as a femoral artery, and so that the distal attachment region 682 can be longitudinally and rotationally manipulated. The thin-walled metal tube 615 extends through the introducer 600 to the manipulation section 680, terminating at a connection means 616.

The connection means 616 is adapted to accept a-syringe to facilitate the introduction of medical reagents into the thin-walled metal tube 615. The thin-walled metal tube 615 is in fluid communication with the apertures 612 of the flexible extension 611. Therefore, medical reagents introduced into connection means 616 will flow to and emanate from the apertures 612.

A plastic tube 641 is coaxial with and radially outside of the thin walled metal tube 615. The plastic tube 641 is "thick-walled"-its wall is preferably several times thicker than that of the thin-walled metal tube 615. A sheath 630 is coaxial with and radially outside of the plastic tube 641. The thick-walled plastic tube 641 and the sheath 630 extend distally to the manipulation region 680.

During the placement phase of the medical procedure, the stent graft 400 is retained in a compressed condition by the sheath 630. The sheath 630 extends distally to a gripping and hemostatic sealing means 635 of the external manipulation section 680. During assembly of the introducer 600, the sheath 630 is advanced over the cylindrical sleeve 610 of the proximal attachment region 684 while the stent graft 400 is held in a compressed state by an external force. A distal attachment (retention) section 640 is coupled to the thick-walled plastic tube 641. The distal attachment section 640 retains the distal ends 407 of the stent graft 400 during the procedure. Likewise, the cylindrical sleeve 610 retains the anchoring stents 422. The distal ends 407 of the stent graft 400 have a loop (not shown) through which a distal trigger wire (not shown) extends. The distal trigger wire extends through an aperture (not shown) in the distal attachment section 640 into an annular region between the thin-walled tube 615 and the thick-walled tube 641. The distal trigger wire extends through the annular space to the manipulation region 680. The distal trigger wire exits the annular space at a distal wire release mechanism 625.

The external manipulation section 680 includes a hemostatic sealing means 635. The hemostatic sealing means 635 includes a hemostatic seal (not shown) and a side tube 629. The hemostatic sealing means 635 also includes a clamping collar 626 that clamps the sheath 630 to the hemostatic seal, and a silicone seal ring (not shown) that forms a hemostatic seal around the thick-walled plastic tube 641. The side tube 629 facilitates the introduction of medical reagents between the thick-walled tube 641 and the sheath 630.

A proximal portion of the external manipulation section 680 includes a release wire actuation section that has a body 636. The body 636 is mounted onto the thick-walled plastic tube 641. The thin-walled tube 615 passes through the body 636. The distal wire release mechanism 625 and the proximal wire release mechanism 624 are mounted for slidable movement onto the body 636.

The positioning of the proximal and distal wire release mechanisms 624 and 625 is such that the proximal wire release mechanism 624 must be moved before the distal wire release mechanism 625 can be moved. Therefore, the distal ends 407 of the stent graft 400 cannot be released until the anchoring stents 422 have been released, and the barbs 423 have been anchored to the lumen. Clamping screws 637 prevent inadvertent early release of the stent graft 400. A hemostatic seal (not shown) is included so that the release wires can extend out through the body 636 without unnecessary blood loss during the medical procedure.

A distal portion of the external manipulation section 680 includes a pin vise 639. The pin vise 639 is mounted onto the distal end of the body 636. The pin vise 639 has a screw cap 646. When screwed in, vise jaws (not shown) of the pin vise 639 clamp against or engage the thin-walled metal tube 615. When the vise jaws are engaged, the thin-walled tube 615 can only move with the body 636, and hence the thin-walled tube 615 can only move with the thick-walled tube 641. With the screw cap 646 tightened, the entire assembly can be moved together as one piece.

The stent graft 400 is preferably inserted by an introducer 600 via percutaneous entry femoral artery, and then advanced into the desired position over a stiff wire guide using endoluminal interventional techniques. For example, a guide wire (not shown) is first introduced into a femoral artery of the patient and advanced until its tip is beyond the desired deployment region of the stent graft 400. At this stage; the introducer assembly 600 is fully assembled, and ready for introduction into the patient. The stent graft 400 is retained at one end by the cylindrical sleeve 610 and the other by the distal attachment sections 640, and compressed by the sheath 630. In addition, the introducer assembly 600 can be inserted through a femoral artery over the guide wire, and positioned by radiographic techniques, which are not discussed here.

Once the introducer assembly 600 is in the desired deployment position, the sheath 630 is withdrawn to just proximal of the distal attachment section 640. This action releases the middle portion of the stent graft 400 so that it can expand radially. The anchoring stents 422, however, are still retained within the cylindrical sleeve 610 and the distal ends 407 are still retained within the external sheath 630.

Next, the pin vise 639 is released to allow small movements of the thin-walled tube 615 with respect to the thick-walled tube 641. These movements allow the stent graft 400 to be lengthened or shortened or rotated or compressed for accurate placement in the desired location within the lumen. Radiopaque markers (not shown) may be placed along the stent graft 400 to assist with placement of the prosthesis.

When the proximal end 406 of the stent graft 400 is in place, the proximal trigger wire is withdrawn by distal movement of the proximal wire release-mechanism 624. The proximal wire release mechanism 624 and the proximal trigger wire can be completely removed by passing the proximal wire release mechanism 624 over the pin vise 639, the screw cap 646, and the connection means 616. Next, the screw cap 646 of the pin vise 639 is loosened, after which the thin-walled tube 615 can be pushed in a proximal direction to move the cylindrical sleeve 610 in a proximal direction. When the cylindrical sleeve 610 no longer surrounds the anchoring stents 422, the self-expanding stents 422 expand. When the anchoring stents 422 expand, the barbs 423 grip the walls of the lumen to hold the proximal end 206 in place. From this stage on, the proximal end 406 of the stent graft 400 cannot be moved again.

Once the proximal end 406 is anchored, the external sheath 630 is withdrawn to distal of the distal attachment section 640. This withdrawal allows the shorter leg 421 and the longer leg 420 of the stent graft 400 to expand. At this point, the distal ends 407 of the stent graft 400 may still be moved. Consequently, the stent graft 400 can still be rotated or lengthened or shortened for accurate positioning. Such positioning of the stent graft 400 may ensure that the shorter leg 421 extends in the direction of a contralateral artery.

The introducer 600 and the deployment method described above can be adapted for implantation in other regions. In addition, a simpler variation of the introducer 600 may be used to introduce the suture-free bifurcated stent graft 400. This simpler variation of the introducer 600 may be based on the same principles as the introducer 600 described above, but may be less complex.

Figure 8:
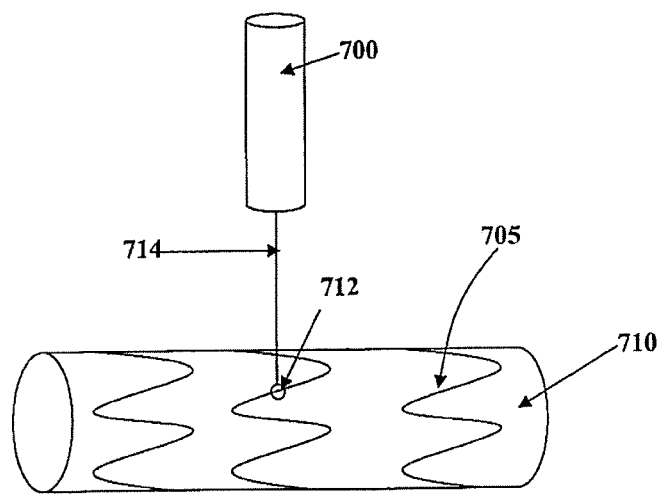
FIG. 8 shows a schematic view of a laser for creating thermoplastically fused regions to directly attach a stent and a woven graft.

FIG. 8 shows a schematic view of a laser 700 for creating thermoplastically fused regions to directly attach a stent 705 and a woven graft 710.

Lasers provide another method of heating the stent 705 and/or the graft material 710; to directly attach the woven graft 710 and the stent 705 at a thermoplastically fused region 712. This process may be referred to as laser welding. In one embodiment, in which the stent 705 is located on the exterior of the woven graft 710, a laser beam 714 generated by the laser 700 may be directed at a desired location of the stent 705. This in turn may increase the temperature of the stent 705 at the desired location. The temperature to which the stent 705 is heated can be controlled by a number of factors, including the type of laser used, the wavelength of the laser and the amount of time the laser is directed at the stent 705. During this process, the stent 705 may or may not be in contact with the woven graft 710. In one embodiment, the stent 705 may be heated in this manner and then brought into contact with the woven graft 710. In another embodiment, the stent 705 may be in contact with the woven graft 710 while the stent 705 is being heated by the laser 700, such that the graft 710 will undergo thermoplastic deformation to produce a thermoplastically fused region when the stent 705 reaches the desired temperature.

In another embodiment, the laser beam 714 may be directed at a desired location on the woven graft 710. This in turn may increase the temperature of the woven graft 710 at the desired location. The temperature to which the woven graft 710 is heated can be controlled by a number of factors, including the type of laser used, the wavelength of the laser and the amount of time the laser is directed at the woven graft 710. The woven graft 710 is heated with the laser 700 until sufficient thermoplastic deformation of the graft material has occurred to provide a thermoplastically fused region, thus directly attaching the woven graft 710 and the stent 705. In one embodiment, this process of plastic deformation may be carried out where the stent 705 is located on the exterior of the woven graft 710. In another embodiment, this process of plastic deformation may be carried out where the stent 705 is located on the interior of the woven graft 710.

A variety of lasers maybe employed for this purpose, including $CO_2$ and Nd:YAG lasers. In addition, a variety of laser wavelengths may also be utilized. The selection of a specific type of laser and of a wavelength will depend on the physical properties of the stent 705, the physical properties of the woven graft 710 and the temperatures necessary to achieve thermoplastic deformation of the woven graft 710.

Due to the precision with which such lasers can be operated, this approach may also allow for formation of precisely located thermoplastically fused regions which directly attach the woven graft 710 and the stent 705. That is, for example, the stent 705 and the woven graft 710 may be attached to the stent 705 at desired points, along the stent 705 or the woven graft 710 may be attached to the stent 705 along the entire length of the stent 705. Moreover, the utilization of lasers for this process may also provide an efficient means for automating the process of directly attaching the stent 705 and the woven graft 710.

It is not excluded that a part of the structural component or components may be sutured to the graft material and another part fused thereto.

It is intended that the foregoing detailed description be regarded as illustrative rather than limiting.

The invention claimed is:

1. An endovascular prosthesis, comprising:
at least one stent, and
a woven graft material having a length and a circumference,
wherein the at least one stent is connected to the graft material by direct attachment of the at least one stent to the graft material at thermoplastically fused regions of the graft material, and wherein the at least one stent comprises a stent segment,
wherein the thermoplastically fused regions are disposed along the entire length and about the entire circumference of the of the graft material and comprise 30% or less of the graft material,
wherein the thermoplastically fused regions are melted regions of graft material that have lost some or all of its woven attributes, wherein the remainder of the graft material retains its woven attribute,
wherein the graft material comprises a first surface, a second surface and an interior region therebetween; each stent segment comprises a length and four sides, wherein the four sides consist of: a graft material contacting face, which is substantially parallel to and in contact with the second surface; a first edge and a second edge, wherein the first and second edges are on opposite sides of the at stent segment and are substantially perpendicular to the contacting face; and an opposing face, which is located on the opposite side of the one stent segment from the contacting face, and
wherein the contacting face, the first edge and the second of each stent segment are substantially enclosed by one of the thermoplastically fused regions.

2. The endovascular prosthesis of claim 1, wherein the graft material has an interior and an exterior the at least one stent is directly attached to the exterior of the graft material.

3. The endovascular prosthesis of claim 1, wherein the graft material comprises a biocompatible polyester.

4. The endovascular prosthesis of claim 3, wherein the graft material comprises polyethylene terephthalate.

5. The endovascular prosthesis of claim 1, wherein the thermoplastically fused regions are formed by passing an electric current through each stent segment.

6. The endovascular prosthesis of claim 1, wherein the thermoplastically fused regions are formed using laser welding.

7. The endovascular prosthesis of claim 1, wherein each thermoplastically fused regions:
extends between the first surface and the second surface; and
is adhered to the contacting face, the first edge and the second edge along the length of the one stent segment.

8. The endovascular prosthesis of claim 1, wherein the thermoplastically fused regions:
extend between the first surface and the second surface; and
are adhered to the contacting face, the first edge, the second edge and the opposite face of each stent segment.

9. The endovascular prosthesis of claim 1, wherein the thermoplastically fused regions extends from the first surface to the second surface.

10. The endovascular prosthesis of claim 1, wherein the graft material comprises a single material, a blend of materials, a laminate or a composite of two or more materials.

11. The endovascular prosthesis of claim 1, wherein the thermoplastically fused regions comprise 10% or less of the graft material.

12. An endovascular prosthesis, comprising:
- a woven graft material having a proximal end, a distal end, a length from the proximal end to the distal end, a circumference, a luminal surface and an abluminal surface;
- a structural component supporting the length and circumference of the woven graft material, the structural component selected from the group consisting of a stent extending from the proximal end to the distal end and a plurality of stents along the length of the woven graft material;
- wherein the stent or the plurality of stents are connected to the graft material along its entire length and circumference by direct attachment of the stent or plurality of stents to the graft material at thermoplastically fused regions along the entire length and about the entire circumference of the graft material;
- wherein the thermoplastically fused regions are disposed along the entire length and circumference of the of the graft material and comprise 30% or less of the graft material,
- wherein the thermoplastically fused regions are melted regions of graft material that have lost some or all of its woven attributes, and
- wherein the remainder of the graft material retains its woven attribute,
- wherein the graft material comprises an interior region between the abluminal and luminal surfaces, and wherein the stent or the plurality of stents comprises a stent segment having a length and four sides, wherein the four sides consist of: a contacting face, which is substantially parallel to and in contact with the abluminal surface; a first edge and a second edge, wherein the first and second edges are on opposite sides of the stent segment and are substantially perpendicular to the abluminal surface and the contacting face; and an opposing face, which is located on the opposite side of the stent segment from the contacting face, and
- wherein the contacting face, the first edge and the second edge of each stent are substantially enclosed by a thermoplastically fused region of the thermoplastically fused regions.

13. The endovascular prosthesis of claim 12, wherein the structural component comprises a series of unconnected stents disposed along the length of the graft material.

14. The endovascular prosthesis of claim 12, wherein the structural component comprises a single stent disposed along the length of the graft material.

15. The endovascular prosthesis of claim 12, wherein the prosthesis is free of any other attachment between the stent or plurality of stents and the graft material.

* * * * *